United States Patent
Baumann et al.

(10) Patent No.: US 7,564,941 B2
(45) Date of Patent: *Jul. 21, 2009

(54) FOCUS-DETECTOR ARRANGEMENT FOR GENERATING PROJECTIVE OR TOMOGRAPHIC PHASE CONTRAST RECORDINGS WITH X-RAY OPTICAL GRATINGS

(75) Inventors: Joachim Baumann, München (DE); Christian David, Lauchringen (DE); Martin Engelhardt, München (DE); Jörg Freudenberger, Eckental (DE); Eckhard Hempel, Fürth (DE); Martin Hoheisel, Erlangen (DE); Thomas Mertelmeier, Erlangen (DE); Franz Pfeiffer, Brugg (CH); Stefan Popescu, Erlangen (DE); Manfred Schuster, München (DE)

(73) Assignee: Siemens Aktiengesellschaft, Munich (DE)

( * ) Notice: Subject to any disclaimer, the term of this patent is extended or adjusted under 35 U.S.C. 154(b) by 176 days.

This patent is subject to a terminal disclaimer.

(21) Appl. No.: 11/700,154

(22) Filed: Jan. 31, 2007

(65) Prior Publication Data
US 2007/0183582 A1 Aug. 9, 2007

(30) Foreign Application Priority Data

| Feb. 1, 2006 | (DE) | ..................... 10 2006 004 604 |
| Feb. 1, 2006 | (DE) | ..................... 10 2006 004 976 |
| Aug. 9, 2006 | (DE) | ..................... 10 2006 037 254 |

(51) Int. Cl.
*A61B 6/00* (2006.01)

(52) U.S. Cl. .............................. 378/19; 378/62; 378/146

(58) Field of Classification Search .................. 378/19, 378/62, 84, 85, 145, 146; 359/558
See application file for complete search history.

(56) References Cited

U.S. PATENT DOCUMENTS 5,812,629 A 9/1998 Clauser (Continued)

FOREIGN PATENT DOCUMENTS

DE 10 2006 015 355.3 8/2007

(Continued)

OTHER PUBLICATIONS

Weitkamp et al., "X-ray phase imaging with a grating interferometer", Optics Express 2005, vol. 12, No. 16, pp. 6296-6304.

(Continued)

*Primary Examiner*—Courtney Thomas
(74) *Attorney, Agent, or Firm*—Harness, Dickey & Pierce, P.L.C.

(57) ABSTRACT

A focus-detector arrangement of an X-ray apparatus is disclosed for generating projective or tomographic phase contrast recordings with a phase grating. According to at least one embodiment of the invention, in the gaps between its bars, the phase grating includes a filler material whose linear attenuation coefficient in the relevant energy range is greater than that of the bars. The height of the filler material in the gaps is dimensioned on the one hand so that the X-radiation with the energy used for measuring the phase shift generates a phase shift in the X-radiation such that, after the phase grating, the rays which pass through the bars are phase shifted by one half wavelength relative to the rays which pass through the gaps with the filler material. Further, the height of the filler material in the gaps on the other hand is dimensioned so that the attenuation of the X-radiation, at least in relation to the energy used for measuring the phase shift, is the same when passing through the bars and when passing through the filler material.

19 Claims, 6 Drawing Sheets

U.S. PATENT DOCUMENTS

| | | | |
|---|---|---|---|
| 2003/0081316 A1 | 5/2003 | Goldberg et al. | |
| 2005/0207012 A1 | 9/2005 | Arnold et al. | |
| 2007/0183584 A1* | 8/2007 | Baumann et al. | 378/145 |

FOREIGN PATENT DOCUMENTS

| | | |
|---|---|---|
| DE | 10 2006 015 356.1 | 8/2007 |
| DE | 10 2006 015 358.8 | 8/2007 |
| DE | 10 2006 017 290.6 | 8/2007 |
| DE | 10 2006 017 291.4 | 8/2007 |
| EP | 1 447 046 A1 | 8/2004 |

OTHER PUBLICATIONS

D. Vaughan (ed.), "X-Ray Data Booklet", Lawrence Berkeley Laboratory, Berkley, 1986, pp. 2-28, 2-29.

U. Bonse and M. Hart, "An X-ray Interferometer", Appl. Phys. Lett., 1965, vol. 6, No. 8, pp. 155-156.

Ingal and Beliaevskaya, "X-ray plane-wave topography observation of the phase contrast from a non-crystalline object", J. Phys. D: Appl. Phys. 28, 1995, pp. 2314-2317.

R. Fitzgerald, "Phase-Sensitive X-Ray Interferometer", Physics Today, 53, 2000, pp. 23-26.

Chapman et al., "Diffraction enhanced x-ray imaging", Phys. Med. Biol. 42, 1997, pp. 2015-2025.

Wilkins et a., "Phase-contrast imaging using polychromatic hard X-rays", Nature 384, 1996, pp. 335-338.

V. Lehmann, The Physics of Macropore Formation in low Doped n-Type Silicon, J. Electrochemical Soc. 140 (10), 1993, pp. 2836-2843.

Bergmann, Schäfer, "Lehrbuch der Experimentalphysik", vol. 1, Mechanik, Akustik, Wärme, De Gruyter, Berlin, 1970, pp. 542-554.

Shack et al., J. Opt. Soc. Am. 61, 1971, p. 656.

Platt et al., "History and Principles of Shack-Hartmann Wavefront Sensing", Journal of Refractive Surgery, vol. 17, 2001, pp. 573-577.

F. Roddier, "Variations on a Hartmann theme", Opt. Eng. 29, 1990, pp. 1239-1242.

Primot et al., "Deconvolution from wave-front sensing: a new technique for compensating turbulence-degraded images", J. Opt. Soc. Am. 7(9), 1990, pp. 1598-1608.

J. C. Wyant, "White Light Extended Source Shearing Interferometer", Appl. Opt. 13, 1974, pp. 200-202.

C. L. Koliopoulos, "Radial grating lateral shear heterodyne interferometer", Appl. Opt. 19, 1980, pp. 1523-1528.

J. Primot, L. Songo, "Achromatic three-wave (or more) lateral shearing interferometer", J. Opt. Soc. Am. A, 12(12), 1995, pp. 2679-2685.

J. Primot, "Theoretical description of Shack-Hartmann wave-front sensor", Optics Communications, 222, 2003, pp. 81-92.

V. Ronchi, "Forty Years of History of a Grating Interferometer", Appl. Opt., 3(4), 1964, pp. 437-451.

Schroer et al., "Hard x-ray nanoprobe based on refractive x-ray lenses", Appl. Phys. Lett. 87, 124103, 2005.

M. Bavdaz, N. Gurker, "Coded Imaging X-ray Microprobe", X-Ray Spectrometry, 22, 1993, pp. 65-70.

C. J. Kotre, I. P. Birch, "Phase contrast enhancement of x-ray mammography: a design study", Phys. Med. Biol., 44, 1999, pp. 2853-2866.

Arfelli et al, "Low-dose phase contrast x-ray medical imaging", Phys. Med. Biol. 43, 1998, pp. 2845-2852.

Herrlin et al., "Contrast-Enhanced Radiography by Differential Absorption Using a Laser-Produced X-Ray Source", Investigative Radiology 32, 1997, pp. 306-310.

Grätz et al.,"Time-Gated Imaging in Radiology: Theoretical and Experimental Studies", IEEE J. of selected Topics in Quantum Electronics, 2(4), 1996, pp. 1041-1048.

Murnane et al., "Ultrafast X-ray Pulses from Laser-Produced Plasmas", Science, vol. 251, 1991, pp. 531-536.

Krol et al., "Laser-based microfocused x-ray source for mammography: Feasibiliy study", Med. Phys. 24(5), 1997, pp. 725-732.

Piestrup et al., "A design of mammography units using a quasiminichromatic x-ray source", Review of Scientific Instruments, 72(4), 2001, pp. 2159-2170.

C. G. Schroer, B. Lengler, "Focusing Hard X Rays to Nanometer Dimensions by Adiabatically Focusing Lenses", Phys. Rev. Lett. 94, 054802, 2005.

Weitkamp et al.: X-ray phase imaging with a grating interferometer Optic Express 12 (16),2005 p. 6296-6304.

"Tomographic Image Reconstruction Using X-Ray Phase Information" by Momose et al., 1996.

" Time-Gated Medical Imaging with Ultrafast Laser Plasma X-Rays" by Barty et al., 1995.

* cited by examiner

FOCUS-DETECTOR ARRANGEMENT FOR GENERATING PROJECTIVE OR TOMOGRAPHIC PHASE CONTRAST RECORDINGS WITH X-RAY OPTICAL GRATINGS

PRIORITY STATEMENT

The present application hereby claims priority under 35 U.S.C. § 119 on German patent application numbers DE 10 2006 004 604.8 filed Feb. 1, 2006, DE 10 2006 004 976.4 filed Feb. 1, 2006, and DE 10 2006 037 254.9 filed Aug. 9, 2006, the entire contents of each of which is hereby incorporated herein by reference.

FIELD

Embodiments of the invention generally relate to a focus-detector arrangement of an X-ray apparatus for generating projective or tomographic phase contrast recordings of a subject. For example, it may relate to one having a radiation source for generating X-radiation and irradiating the subject, a phase grating arranged behind the subject, which generates an interference pattern of the X-radiation in a predetermined energy range, and an analysis-detector system which detects at least the interference pattern generated by the phase grating in respect of its phase shift with position resolution.

BACKGROUND

Focus-detector arrangements for generating projective or tomographic phase contrast recordings of a subject are widely known. By way of example, reference is made to the European patent application EP 1 447 046 A1 and the German patent applications (not yet published that the priority date of the present application) with the file references 10 2006 017 290.6, 10 2006 015 358.8, 10 2006 017 291.4, 10 2006 015 356.1 and 10 2006 015 355.3.

For imaging by ionizing rays, in particular X-rays, principally two effects can be observed which occur when the radiation passes through matter, namely absorption and the phase shift of the radiation passing through a subject. It is known that in many cases, the phase shift when a ray passes through a subject reacts much more strongly to small differences in the thickness and composition of the penetrated matter than the absorption effects do. For such phase contrast radiography or phase contrast tomography, the phase shift due to the object must be evaluated. Here, similarly as conventional absorption contrast X-radiography or absorption contrast X-ray tomography, both projective images of the phase shift can be compiled or even tomographic representations of the phase shift can be calculated from a multiplicity of projective images.

The phase of an X-ray wave cannot be determined directly, rather only by interference with a reference wave. The phase shifts relative to reference waves or neighboring rays can be measured by using interferometric gratings. In respect of interferometric measurement methods, reference is made to the documents cited above. In these methods, coherent X-radiation is passed through a subject, then delivered through a phase grating with a bar height adapted to the radiation so as to create an interference pattern, which depends on the phase shift occurring in the object. This interference pattern is measured by a subsequent analysis-detector arrangement, so that the phase shift can be determined with position resolution.

The following should essentially be pointed out in this regard:

The emission of X-ray photons from laboratory X-ray sources (X-ray tubes, secondary targets, plasma sources, radioactive sources) as well as by conventional synchrotron radiation sources of the first to third generations is subject to stochastic processes. The emitted X-radiation therefore has no spatial coherence per se. In phase contrast radiography and tomography or any interference experiment, however, the radiation of X-ray sources behaves as coherent radiation when the observation angle at which the source appears to the observer or the object, the grating or the detector, is sufficiently small. The so-called spatial coherence length $L_c$ can be provided as a measure of the spatial or transverse coherence of an extended X-ray source $$L_c = \lambda \frac{a}{s}. \tag{1}$$

Here, $\lambda$ is the wavelength, s is the transverse source size and a is the source-observation point distance. Many authors also refer to half the above-defined value as the spatial coherence length. The exact value is incidental; what is important is that the coherence length $L_C$ is large compared to the (transverse) dimension of the spatial region from which rays are intended to interfere with one another.

In the context of the patent application, the term coherent radiation is intended to mean radiation which leads to the formation of an interference pattern under the given geometries and given distances of the X-ray optical gratings. It is self evident that the spatial coherence and therefore the spatial coherence length is always determined by the trio of quantities: wavelength, source size and observation distance. With a view to compact formulation, this fact has been abbreviated to terms such as "coherent X-radiation", "coherent X-radiation source" or "point source for generating coherent X-radiation". The basis for these abbreviations is that the wavelength or the energy E of the X-radiation in the applications discussed here is limited by the desired penetratability of the subject on the one hand and the spectrum available in laboratory X-ray sources on the other hand. The distance a between the source and the observation point is also subject to certain restrictions in laboratory equipment for nondestructive material testing or medical diagnosis. This usually leaves only the source size s as a single degree of freedom, even though the relationships between source size and tube power set narrow limits here.

The requirement for a small or point-like radiation source means that the available intensity is also relatively low. In order to increase the intensity, it has therefore also been proposed to use an X-ray source with a relatively large-area focus and to place an X-ray optical absorption grating, a so-called source grating, in the beam path between the focus and the subject. The large-area focus makes it possible to use larger and therefore more powerful X-ray sources. The narrow slits or gaps of the source grating ensure that all the rays, which have to emerge from the same slit, comply with the requisite spatial coherence. The slit width must satisfy the size requirement given by Equation (1) for the transverse source size s. Correct superposition, at least in terms of intensity, of the maxima and minima of the standing wave field is possible between the photons from slit to slit of the source grating with suitable tuning of the source grating period g0 and the interference pattern period $g_2$ as well as the distance l between the source grating $G_0$ and the phase grating $G_1$ and the distance d between the phase grating $G_1$ and the interference pattern, according to $$g_0/g_2 = 1/d. \quad (2)$$

In the abbreviated formulation of the patent application, the term "quasi-coherent radiation" or "quasi-coherent radiation source" is used in this context.

The temporal or longitudinal coherence of the radiation is associated with the monochromaticity of the X-radiation or of the X-radiation source. The X-radiation of intense characteristic lines usually has a sufficient monochromaticity or temporal coherence length for the applications discussed here. Upstream monochromators or selection of the resonant energy via the bar height of the phase grating can also filter out a sufficiently narrow spectral range from a Bremsstrahlung spectrum or synchrotron spectrum, and thus satisfy the requirements for the temporal coherence length in the present arrangements.

A problem with this measurement of the interference patterns is that interference phenomena occurring as significantly as possible behind the phase grating are required, in order to be able to measure them with sufficient accuracy. When using a normal X-ray tube, however, a broad spectrum of X-radiation is generally delivered, while only radiation of a limited energy range contributes to generating the phase shift-induced interference patterns. There is sometimes therefore a relatively high background noise relative to the interference patterns to be measured.

SUMMARY

In at least one embodiment of the invention to provide a focus-detector arrangement for generating projective or tomographic phase contrast recordings with the aid of phase gratings, which generates a maximally pronounced interference pattern.

The Inventors, in at least one embodiment, have discovered that at least one contribution to generating maximally strong interference patterns, and therefore as great as possible a signal-to-noise ratio of the phase measurements in a focus-detector arrangement, can be achieved if the intensity contributions of the interfering radiation components are as far as possible equal in size. It has furthermore been discovered that when the radiation passes through a phase grating, this situation can be achieved precisely when the phase grating, which as is known consists of a multiplicity of periodically arranged grating bars and gaps existing between the grating bars, is designed so that on the one hand a phase change of $\pi$ or $\lambda/2$ occurs between neighboring rays which pass through the bars and gaps, as a basic condition for creation of the interference pattern, but on the other hand the intensity of the radiation behind the gap and the radiation behind the bar is also as equal as possible.

To this end the Inventors propose, in at least one embodiment, that the phase grating be configured, in respect of bar height and a filler material lying in the grating gaps, so as to obtain both the desired phase change and an identical attenuation of the radiation, regardless of whether it passes through the bars or the gaps with the filler material.

Accordingly, the Inventors propose, in at least one embodiment, that a focus-detector arrangement known per se of an X-ray apparatus for generating projective or tomographic phase contrast recordings of a subject, consisting of at least: a radiation source for generating X-radiation and irradiating the subject, a phase grating arranged behind the subject, which generates an interference pattern of the X-radiation in a predetermined energy range, and an analysis-detector system which detects at least the interference pattern generated by the phase grating in respect of its phase shift with position resolution, should be improved so that it has the following properties:

in the gaps between its bars, the phase grating should comprise a filler material whose linear attenuation coefficient in the relevant energy range is greater than that of the bars, the height of the filler material in the gaps should be dimensioned on the one hand so that the X-radiation with the energy used for measuring the phase shift generates a phase shift in the X-radiation such that, after the phase grating, the rays which pass through the bars are phase shifted by one half wavelength relative to the rays which pass through the gaps with the filler material, and the height of the filler material in the gaps should on the other hand be dimensioned so that the attenuation of the X-radiation, at least in relation to the energy used for measuring the phase shift, is the same when passing through the bars and when passing through the filler material.

Such matching of the bar height of the grating material to the height of the filler material may readily be carried out by trials with corresponding materials suitable for the production of gratings and for filling the bars. As an alternative, it is naturally also possible to calculate the corresponding heights of the bars and of the filler material analytically from the known absorption coefficients and refractive indices.

So that the radiation, which passes through the grating gaps and the filler material, has a phase difference of $\pi$ or $\lambda/2$ relative to the radiation which passes through the grating bars, the following condition must be satisfied:

$$\delta_F h_F = \delta_S h_S + \delta/2. \quad (3)$$

Here, $\delta_F$ and $\delta_S$ respectively denote the real decrement of the refractive index of the filler material and of the material of the bars, $h_F$ and $h_S$ respectively denote the height of the filler material and of the bars, and $\lambda$ denotes the wavelength of the X-radiation in question.

So that the radiation, which passes through the grating gaps and the filler material, has the same attenuation as the radiation which passes through the grating bars, the following condition must be satisfied:

$$\mu_F h_F = \mu_S h_S. \quad (4)$$

Here, $\mu_F$ and $\mu_S$ respectively denote the absorption coefficients of the filler material and of the material of the bars and $h_F$ and $h_S$ respectively denote the height of the filler material. Strictly speaking, the energy dependency of the absorption coefficients should also be taken into account in this case.

In order to simplify the production of the gratings, the Inventors, in at least one embodiment, furthermore propose to construct the phase gratings from a plurality of sub-gratings arranged in direct succession. This reduces the bar height, usually according to the number of sub-gratings used, so that a simple production processes can also be used.

If a plurality of successively arranged sub-gratings are used, it is furthermore advantageous that, for each of the sub-gratings, the height of the filler material in the gaps be dimensioned so that the X-radiation with the energy used for measuring the phase shift generates a phase shift of $\lambda/2$ in the X-radiation, and that the attenuation of the X-radiation after each sub-grating, at least in relation to the energy used for measuring the phase shift, is the same when passing through the bars and when passing through the filler material in the gaps.

In order to further simplify production, another advantageous embodiment proposes that at least one of the sub-gratings comprises filler material to the height of the bars, at least one of the sub-gratings does not comprise filler material in the gaps, on the one hand the height of the entire filler material in gaps arranged above one another in all the sub-gratings is dimensioned overall so that the X-radiation with the energy used for measuring the phase shift generates a phase shift in the X-radiation of λ/2, and on the other hand the height of the entire filler material of all the sub-gratings is dimensioned overall so that after passing through all the sub-gratings the rays which pass through the sum of the bars arranged successively in the beam direction experience the same intensity loss as the rays which pass through the sum of the gaps with and without filler material arranged successively in the beam direction.

In this way, for example, a sub-grating may be produced with a height which corresponds to the desired overall height of filler material, and this grating may simply be filled therewith, while one or more sub-gratings before and/or after the filled sub-grating may consist only of grating material. In this way, it is thus no longer necessary for the gaps of a grating to be filled uniformly with filler material at a particular height differing from the bar height.

The Inventors have also discovered, in at least one embodiment, that by using a plurality of flat sub-gratings it is possible to reduce the problem of fan-shaped or conical radiation being shadowed on high grating bars with a small gap or bar width, if the sub-gratings arranged successively in the beam direction have different grating periods, the period spacing of the grating periods increasing from at least one sub-grating to at least one subsequent sub-grating and the sub-gratings being arranged aligned with one another so that the rays of the ray beam essentially pass either only through grating gaps or only through grating bars. In the case of perpendicularly arranged bars on flat gratings, it is thus possible to achieve a stepwise approximation to radially aligned bars. In this way, with a set of individual flat sub-gratings respectively with perpendicular bars, it is possible to approximate a grating whose bars are aligned radially overall.

At least one of the gratings—by which is generally meant source gratings, phase gratings, sub-gratings of the phase grating or analyzer gratings—or all the gratings may be designed so that they are flat, or at least one of the gratings or all the gratings may be designed so that they are curved around the radiation origin in at least one plane.

It is also advantageous for at least one of the gratings to include bars and gaps which are aligned radially in the beam direction.

The focus-detector arrangement according to at least one embodiment of the invention may, for example, be used in X-ray systems for generating projective phase contrast recordings, an X-ray C-arc system for generating projective or tomographic phase contrast recordings, or in X-ray computer tomography systems for generating tomographic phase contrast recordings.

BRIEF DESCRIPTION OF THE DRAWINGS

The invention will be explained in more detail below with reference to example embodiments with the aid of the figures, only the features necessary for understanding the invention being represented. Here, the following references are used: 1: computer tomography system; 2: first X-ray tube; 3: first detector; 4: second X-ray tube; 5: second detector; 6: gantry housing; 7: patient; 8: patient support; 9: system axis; 10: control and computation unit; 11: memory; A: material of the grating; a: X-ray after passing through the grating material A; B: material of the grating gap; b: X-ray after passing through the grating gaps and filler material B; d: distance from the phase grating $G_1$ to the analyzer grating $G_2$; $D_1$: detector; E: energy; $E_i$: $i^{th}$ detector element; $F_1$: focus; $G_1$: phase grating; $G_2$: analyzer grating; $G_{11}$, $G_{12}$, $G_{13}$: sub-gratings; $h_{1S}$, $h_{1F}$, $h_{11F}$, $h_{12F}$, $h_{13F}$, $h_{11S}$, $h_{12S}$, $h_{13S}$: height of the bars; $I(E_i(X_G))$: measured intensity at the detector elements $E_i$ with the grating offset $X_G$; $I_{ph}$: measured intensity of the photon flux; $L_C$: coherence length; L: gap in the grating; $Prg_n$: program; S: bar of a grating; $S_i$: X-rays; $X_G$: offset of the analyzer grating or the detector strips; x, z: cartesian coordinates; $\phi_{EX}$: phase of the sinusoidal intensity profile at the detector element $E_X$; $\phi_{ij}$: relative phase shift between the detector elements $E_i$ and $E_j$; λ: wavelength.

In detail.

DETAILED DESCRIPTION OF THE EXAMPLE EMBODIMENTS

Figure 1:
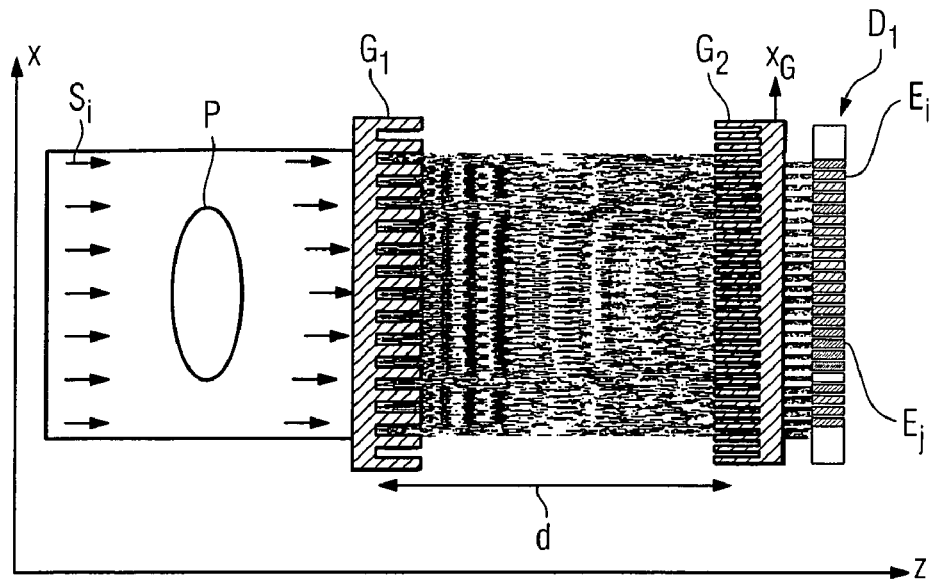
FIG. 1: shows a longitudinal section through an outline representation of a focus-detector arrangement with a phase grating, an analyzer grating and a detector to represent the interference phenomenon for a parallel beam geometry.

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

For better understanding, the basic principle of phase contrast measurement will be firstly described below with FIGS. 1 to 2. In this regard it should essentially be noted that the figures are not shown true to scale, rather they are intended to highlight the basic structure and the described effects. The transverse axis is expanded relative to the longitudinal axis (=optical axis). The angles are therefore represented with an exaggerated size. For didactic reasons, the interference pattern and the analyzer grating in particular have been shown somewhat spatially separated from one another, even though it is precisely the object of the method to position the analyzer grating at the maximum of the interference pattern, i.e. at the Talbot distance. The dimensions d and $r_2$ therefore refer both to the interference pattern and to the analyzer grating.

Figure 2:
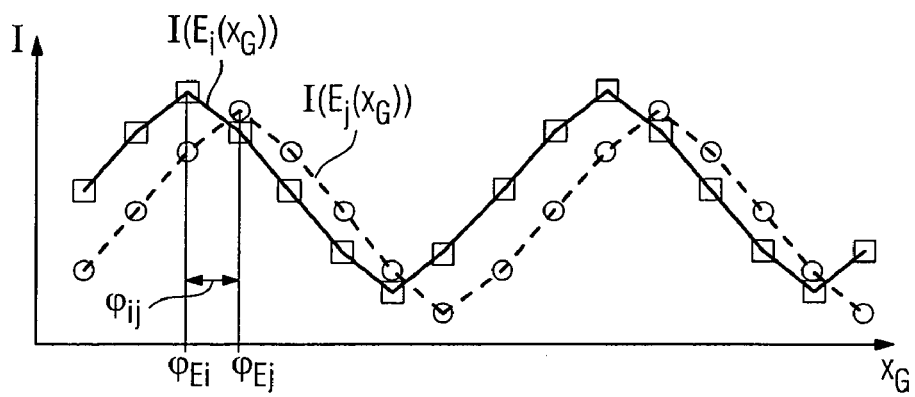
FIG. 2: shows the intensity profile on selected detector elements with a relative displacement of a grating.

FIG. 1 shows coherent radiation coming from the focus or quasi-coherent coming from a source grating, which passes through a sample P, phase shift phenomena taking place after it has passed through the sample P. Owing to the fact that the local gradient of the refractive index of the phase object is imaged when measuring the phase shift, this is also accurately referred to as differential phase contrast imaging.

Here, when passing through the grating $G_1$ an interference pattern is formed at a so-called Talbot distance, which with the aid of the grating $G_2$ leads to different radiation intensities per detector element on the downstream detector $D_1$ and its detector elements. The interference pattern is represented by gray shading in FIG. 1. If the measured intensity of the detector element $E_i$ for example is considered as a function of the relative position $X_G$ of the analyzer grating $G_2$ and the intensity $I_{ph}$ is plotted as a function of the relative position $X_G$, then a sinusoidal profile of the intensity $I(E_i(X_G))$, $I(E_j(X_G))$ is obtained for each detector element $E_i$; $E_j$ as shown in FIG. 2. The phase angle $\phi_{Ei}$, $\phi_{Ej}$ can be determined for each detector element $E_i$; $E_j$ from these functions. Comparing the phase angles $\phi_{Ei}$, $\phi_{Ej}$ of neighboring pixels yields the mutual relative phase shift $\phi_{i,j}$. Relative phase shifts of less than $2\pi$ can be determined in this way. If the phase shift of an object is more than $2\pi$, then, from a region in which there is no phase shift, it is necessary to integrate the differential phase shifts into the desired region as far as the desired position of the object. A projective pixel image or, by corresponding reconstruction methods, even a volume image can be compiled from the phase shifts determined in this way.

The method, in an embodiment, thus uses a phase grating $G_1$ which acts as a diffraction grating and splits the beam into $+1^{st}$ and $-1^{st}$ order beams.

Figure 3:
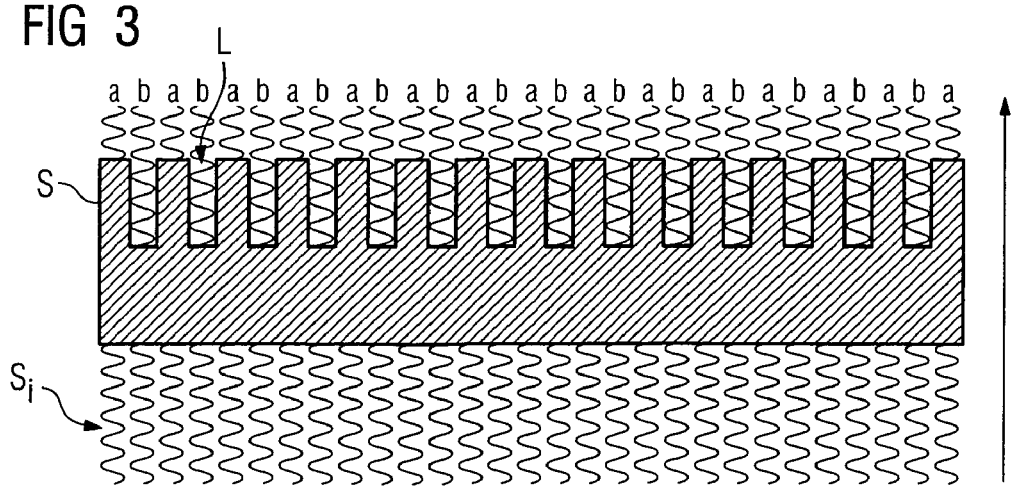
FIG. 3: shows a longitudinal section through a phase grating without filler material in the gaps.

Such a phase grating can be produced by etching rectangular structures in a silicon wafer. One standard technique is dry etching, in which a structure height of 20-50 µm is generally produced at a bar width of 1-2 µm with a period of 2-4 µm. As shown in FIG. 3, the height of the bars is selected so as to obtain a difference of $\pi$ or $\lambda/2$ in the phase shifts of the X-rays transmitted at positions marked by "a" compared with X-rays transmitted at positions marked by "b". If the X-rays transmitted at the positions "a" have the same intensity as the X-rays transmitted at the positions "b" and the grating is fabricated exactly in respect of its other geometrical properties, then the zeroth order diffraction vanishes. If however the wavelength yet because the path length that the X-rays travel through the structure at the positions "a" is slightly longer compared with the positions "b", then the X-rays transmitted at positions "b" have a slightly higher intensity and the zeroth order diffraction does not vanish, even if the grating is fabricated exactly.

In the wave field behind the phase grating, the diffracted rays interfere with one another to form a standing wave field. Objects before or after the phase grating locally influence the local phase shifts, deform the wavefront and modify the amplitude, the phase and the offset of the standing wave field. By using a measurement which provides information about the standing wave field, for instance the amplitude, phase and offset of the standing wave field, it is therefore possible to calculate the influence of the local phase shifts due to the objects before and after the phase grating. In order to scan the wave field with the requisite resolution, an analyzer grating is usually displaced stepwise over the wave field while the intensity per detector element is synchronously monitored.

For each ray in space, the phase shift per ray can therefore be determined by at least three measurements with a respectively offset analyzer grating, from which either the pixel values of a projective recording can be calculated directly in the case of projective X-ray recordings, or projections whose pixel values correspond to the phase shift can be compiled in the case of a computer tomography examination, so that with the aid of reconstruction methods known per se it is possible to calculate therefrom which volume element in the subject is to be ascribed to which component of the measured phase shift. Section images or volume data are thus calculated therefrom, which reflect the local effect of the examined object in respect of the phase shift of X-radiation. Since even minor differences in the thickness or composition of the subject can exert a strong effect on the phase shift, very detailed and high-contrast volume data can thereby be obtained from materials which are relatively similar per se, in particular soft tissue.

This variant of detecting phase shifts of the X-rays which pass through a subject, with the aid of a multiply offset analyzer grating and measuring the radiation intensity on a detector element behind the analyzer grating, means that at least three measurements of each X-ray have to be carried out with a respectively displaced analyzer grating.

In principle, it is even possible to make do without such an analyzer grating and use a detector with sufficiently high position resolution instead, in which case less dose losses occur during the measurement and the phase shift in the relevant ray can be determined by a single measurement.

When using a known grating, such as that shown in FIG. 3, the amplitude of the sinusoidal intensity modulation of the standing wave field is not maximal and for example there is an offset of the minimum intensity of the sinusoidal intensity profile from zero intensity, or the offset is increased.

A problem with the grating according to FIG. 3 is that the rays which pass through the bars and the rays which go through the gaps have different intensities behind the grating, so that optimal formation of the interference pattern desired and to be measured is not obtained.

The position of the interference maxima will therefore be measured less well:

With different positions of the amplitude grating, a position-resolved intensity distribution is measured by the detector. From a plurality of such images, the displacement of the interference pattern caused by the relative phase shift due to the sample is determined. As described above, this may for example be done by displacing the amplitude grating perpendicularly to the grating lines, an image being recorded with a different grating position. If the intensity of the same detector pixel is considered as a function of the grating position, a sinusoidal intensity profile can then be observed. The position of one or more interference maxima of the standing wave field is then determined from the position of this intensity profile, from which the relative phase shift due to the sample can in turn be determined.

The gray value of a detector pixel, which is plotted as a function of the grating position in order to determine the position of one or more interference maxima of the standing wave field, is subject to measurement errors such as noise. This measurement of the position of the standing wave field is thereby impaired.

The measurement described above works commensurately better when the amplitude of the sinusoidal intensity modulation of the standing wave field is larger in relation to the measurement errors.

The expectation value of the deviation (standard deviation) of an actually measured gray value around its expectation value, due to statistical measurement errors, will be referred to below to as noise $\sigma$. With the realistic assumption that this noise consists inter alia of quantum noise, which is proportional to the square root of the expectation value of the number of photons counted, the noise $\sigma$ increases with this number or the expectation value of the gray value of a pixel.

If the measurement time or the source intensity is increased for the measurement described above, then the number of photons counted by a detector pixel increases. The associated quantum noise grows with the square root of this photon count. At the same time, the amplitude of the sinusoidal intensity modulation of the standing wave field increases can proportionally to this photon count, so that in the end the ratio between the amplitude of the sinusoidal intensity modulation of the standing wave field and the measurement errors increases and the measurement described above works better.

But if by using a known grating, such as the one shown in FIG. 3, an offset of the minimum intensity of the sinusoidal intensity profile from zero intensity is incurred or this increases and the amplitude of the sinusoidal intensity modulation of the standing wave field cannot be increased at the same time, then the position of the interference maxima will be measured less well. The offset contains no information, but increases the noise.

Ideally, the interference pattern should therefore have as high as possible an amplitude and the offset of the minimum intensity of the sinusoidal intensity profile from zero intensity should be as small as possible.

This describes only the contribution of the detector to the offset or to the signal-to-noise ratio. This, however, relates only to the offset or the background contributed by the phase grating and the sampling by the analyzer grating. The gaps of the analyzer grating are not arbitrarily narrow; the usual ratio of bar width to gap width is 50:50. Such an analyzer grating therefore averages the measured intensity over a certain width of the interference pattern. An analyzer grating with a bar width to gap width ratio of 90:10 would sample the interference pattern substantially more finely, but at the cost of the number of samples or the measurement time. The residual transmission of the X-radiation by the bars of the grating also has a detrimental effect on the signal-to-noise ratio. For this reason, an analyzer grating width as high as possible an absorption in the grating bars and as low as possible an absorption in the grating gaps is required in order to achieve a high signal-to-noise ratio.

In order to resolve this problem, various alternative solutions of the grating design will be presented below, which may be used individually or in combination with one another.

Figure 4:
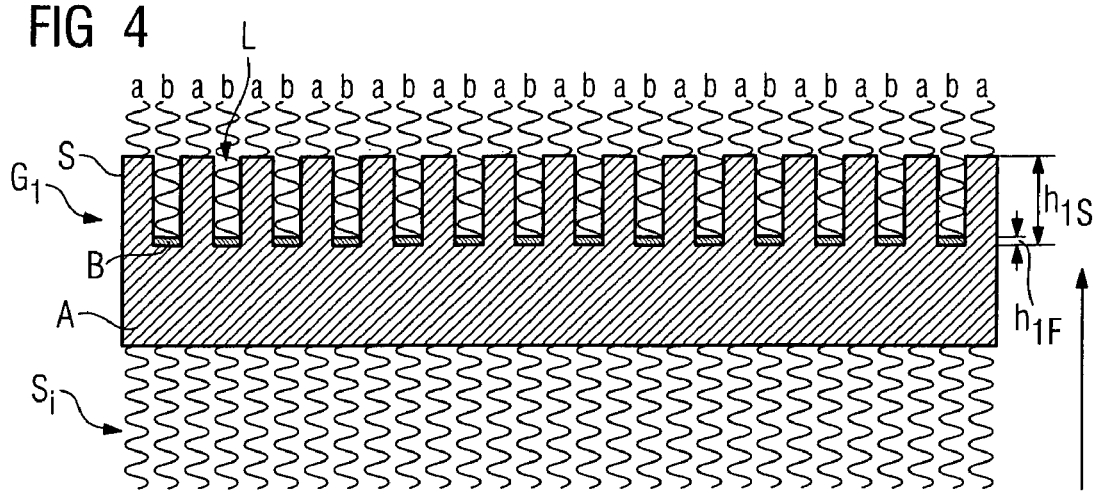
FIG. 4: shows a phase grating according to an embodiment of the invention with filler material in the gaps between the bars.

According to the basic concept of an embodiment of the invention, FIG. 4 firstly shows a simple alternative solution to the problem. A phase grating $G_1$ can be seen here, which has for example been etched from a silicon wafer and comprises bars S of a particular height. The phase grating is configured for a particular X-ray energy E in respect of its effect. Filler material with a high linear attenuation coefficient is introduced into the gaps L of the phase grating $G_1$. The heights $h_{1S}$ and $h_{1F}$ of the grating bar and the filler material are selected, as a function of the material "A" respectively used for the grating and "B" for the filler material, so that the absorption of the X-radiation of the rays "a" and the absorption of the rays "b" is equal, at least in the energy range E to which the phase grating is tuned. At the same time, however, care is taken that the phase shift of the rays "a" and "b" directly at the height of the end of the bars S is shifted by $\pi$ or $\lambda/2$ relative to the ray direction.

In practice, for example, this may be done by sputtering the filler material "B" onto the grating and subsequently chemically-mechanically polishing the surface of the grating, i.e. the ends of the bars.

Figure 5:
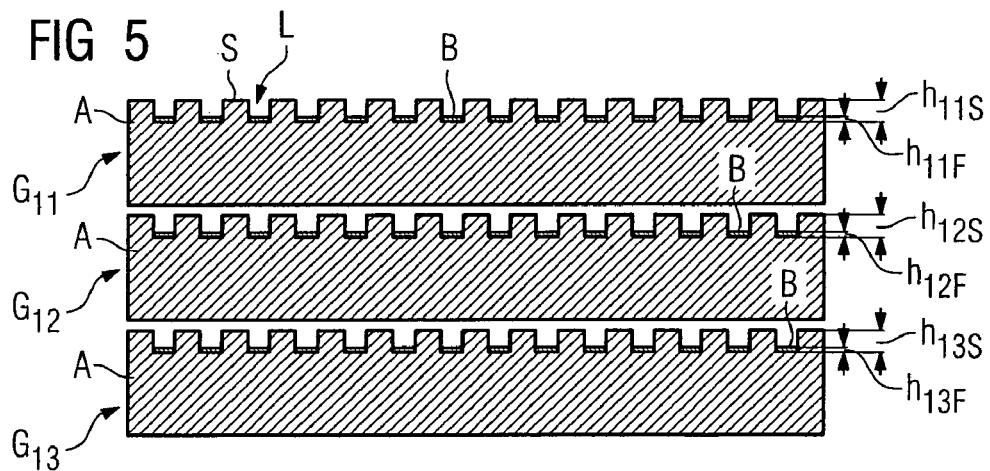
FIG. 5: shows a phase grating according to an embodiment of the invention consisting of three sub-gratings, respectively with filler material in the gaps.

Since the height/width ratio of the bars and gaps, the so-called aspect ratio, is quite large and therefore an elaborate to produce, the invention also proposes to use a plurality of successively arranged diffraction gratings instead of a single diffraction grating. An example of this is shown in FIG. 5. Three gratings $G_{11}$, $G_{12}$ und $G_{13}$ arranged successively and mutually aligned with respect to the bars and gaps are represented here, whose bar height and whose filler material height respectively amount to only one third of the required height. Through an expedient arrangement, the effect of the individual gratings is added together so that the result corresponds to a single grating according to FIG. 4.

Figure 6:
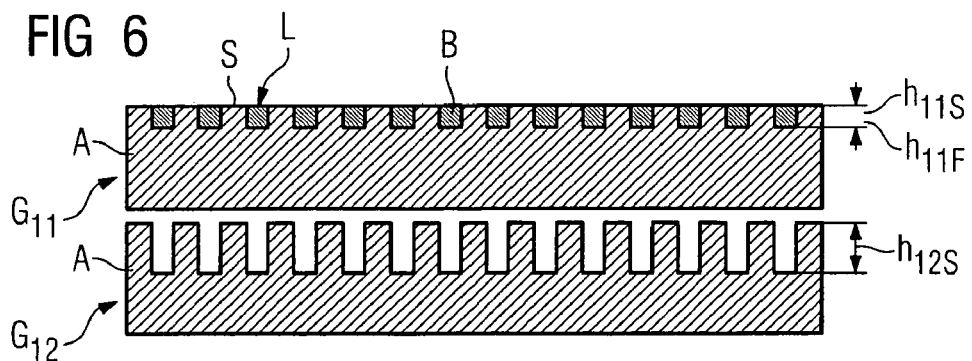
FIG. 6: shows a phase grating according to an embodiment of the invention consisting of two sub-gratings, one grating with gaps entirely filled with filler material and one grating without filler material in the gaps with higher grating bars.

FIG. 6 shows another variant of this embodiment with two additively arranged gratings $G_{11}$ and $G_{12}$, an additional feature to be noted here being that one of the gratings, here the grating $G_{11}$, has a bar height $h_{11S}$ which corresponds to the height of the filler material $h_{11F}$. The required additional height $h_{12S}$ of the bars is achieved by the second grating $G_{12}$, although this is free of filler material. This variant is substantially simpler in terms of production technology and can also be achieved more accurately than filling the gaps with a particular height of filler material, although it serves the same purpose.

It should be pointed out that many different combinations of gratings with the gaps filled, partially filled and empty with different bar heights possible, without departing from the scope of the invention, so long as the basic principle of equal absorption in the region of the bars and gaps is kept. It should furthermore be pointed out that the bars of the gratings in the examples shown are all aligned in one direction, although a reversed alignment or combinations of different alignments are readily possible.

For the case in which the phase gratings according to an embodiment of the invention are intended to be used in conjunction with strongly diverging radiation, i.e. for cone or fan beam geometries, an additional improvement which the Inventors propose when using a plurality of sub-gratings is to use different periods of the individual sub-gratings so as to ensure that a fanned beam passes either only through grating bars or only through grating gaps. Such an example can be seen in FIG. 7. Here, when using a fan beam, three gratings $G_{11}$, $G_{12}$ and $G_{13}$ are shown with a period length increasing in the beam direction, only the last grating $G_{11}$ in the beam direction having the gaps flush-filled with the filler material with a high linear attenuation coefficient. The increase in the period length corresponds to the fanning of the beam at the respective distance from the focus $F_1$. This ensures that the rays denoted by "a" pass only through bars S, while the rays denoted by "b" pass only through the gaps L and optionally the filler material B found there.

It should be pointed out that mutual (pre)alignment of the gratings may be achieved by the use of corresponding markings on the gratings.

Fine adjustment of the gratings may also be carried out piecewise. To this end, a first grating is used. Since it is too thin for an optimal layout, the resulting standing wave field is only poorly pronounced, but nevertheless present. The grating can thus be aligned with the aid of the standing wave field:
1. Alignment of the grating position along the optical axis of the layout: The periods of the phase grating and of the analyzer grating are interlinked, in the case of a cone beam geometry by:

$$g_2 = \frac{1}{2} \frac{r_1 + d}{r_1} g_1 \quad (5)$$

where
d is the distance between the gratings,
$r_1$ is the distance between the source and the first grating, $g_2$ is the period of the analyzer grating $G_2$ (equal to the transverse period of the standing wave field) $g_1$ is the period of the phase grating $G_1$.

If this condition is not fulfilled then an interference pattern is not obtained on a detector placed behind the analyzer grating, but instead a so-called division moiré pattern, consisting of shadow lines which are parallel to the grating bars. This is the case, for example, whenever the phase grating is displaced along the optical axis relative to the intended position. The grating may then be aligned in the position along the beam axis by displacing the phase grating so that this pattern vanishes.

2. Parallel alignment of the grating lines:

If the grating lines of the analyzer grating are not parallel to the standing wave field (and therefore to the grating lines of the beam splitter grating) then an interference pattern is not obtained on a detector placed behind the analyzer grating, but instead a so-called rotation moiré pattern consisting of shadow lines which are perpendicular to the grating bars. The grating lines may then be aligned parallel by rotating the phase grating so that this pattern vanishes.

In practice, a superposition of a rotation and a division moiré pattern can take place. This does not change anything for the principle of aligning the gratings in respect of angle and distance. The grating lines may firstly be aligned parallel by rotating the grating so that a pure division moiré is observed on the detector, i.e. a moiré pattern with shadow lines which are parallel to the grating lines. The spacing of the gratings is then corrected as described above. As an alternative, the grating position may firstly be aligned along the optical axis by displacing the grating until a pure rotation moiré is observed on the detector, i.e. a moiré pattern with shadow lines which are perpendicular to the grating lines. The rotation of the gratings is then corrected as described above.

If a further incorrectly aligned phase grating is added to the correctly aligned gratings, the standing wave field is perturbed. A moiré pattern is then created in the same way as described above. The added phase grating will be aligned in the same way as the first grating. Further gratings are added in the same way.

Figure 8:
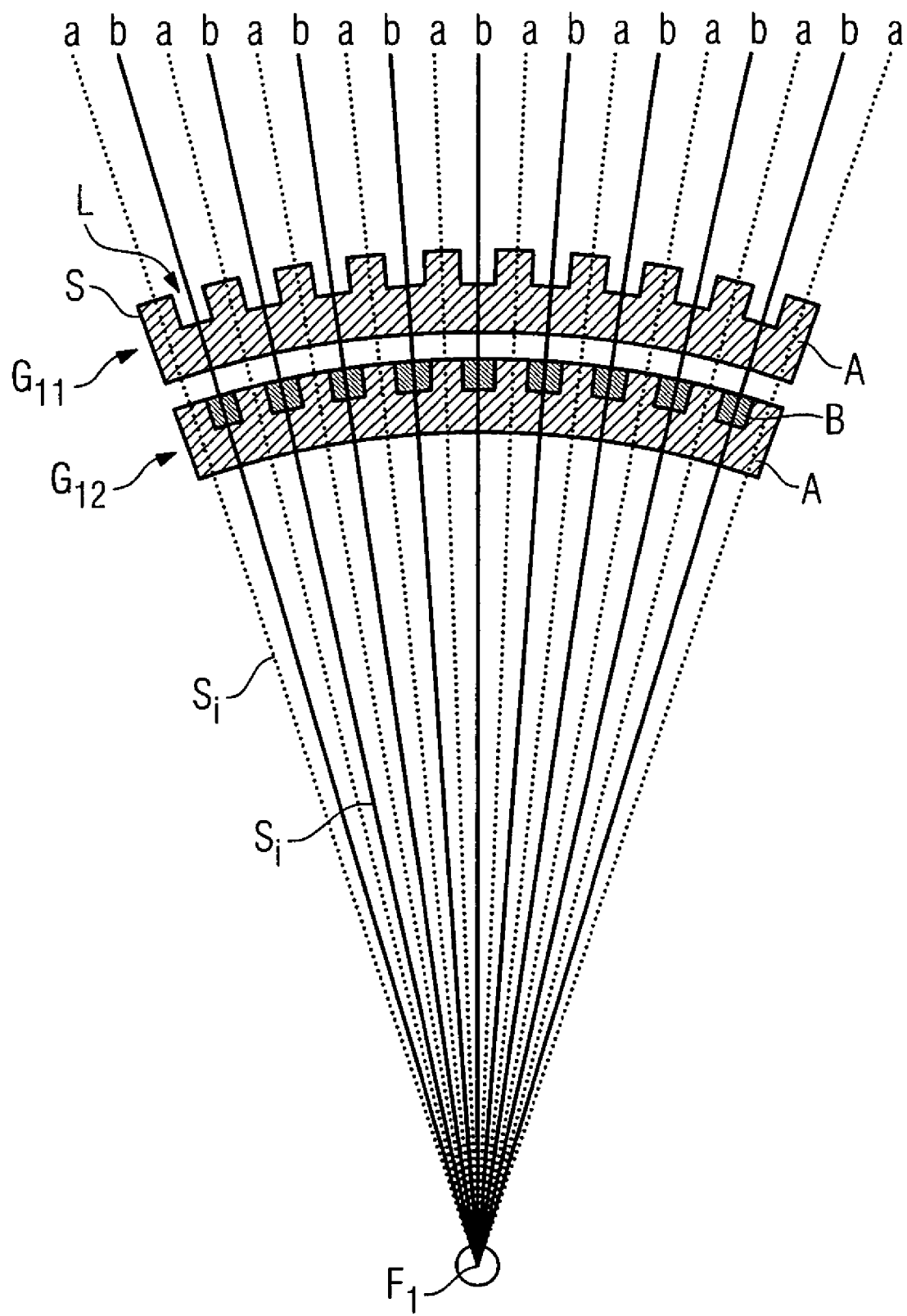
FIG. 8: shows a phase grating according to an embodiment of the invention consisting of two curved sub-gratings, one grating with flush-filled filler material in the gaps and one grating without filler material, the gaps and grating bars of the gratings being radially aligned with one another and respectively between themselves.

FIG. 8 shows another variant of a phase grating including two sub-gratings $G_{11}$ and $G_{12}$, the sub-grating $G_{11}$ here comprising empty gaps and the sub-grating $G_{12}$ comprising gaps flush-filled with filler material. The two sub-gratings are curved concentrically around the focus here, such that the bars S of the individual sub-gratings are also aligned radially with respect to the focus $F_1$ here so that no shadowing of the radiation can occur at the bars S.

Figure 9:
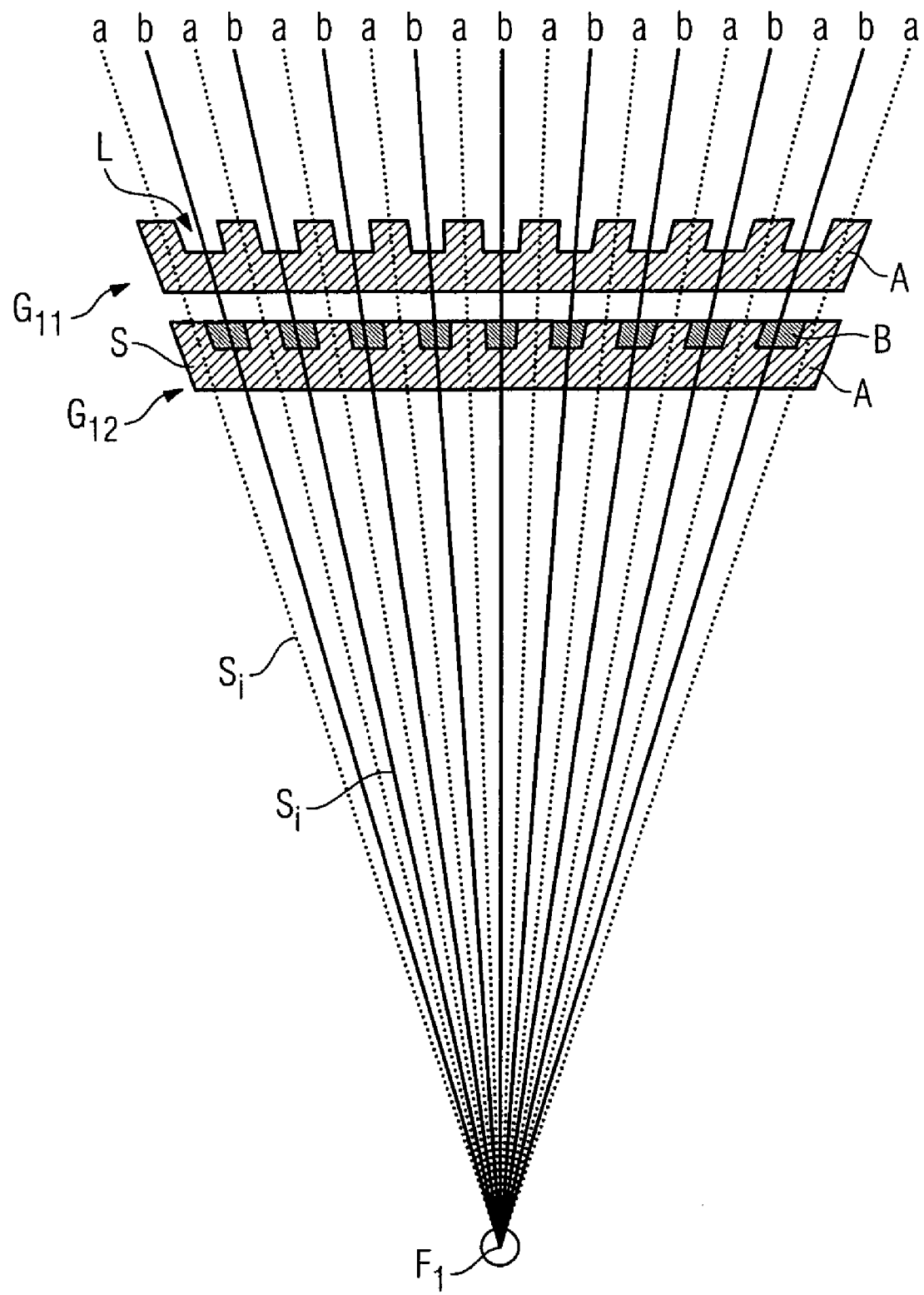
FIG. 9: shows a phase grating according to an embodiment of the invention consisting of two flat sub-gratings, one grating with flush-filled filler material in the gaps and one grating without filler material, the gaps and grating bars of the gratings being radially aligned respectively between themselves.

Another variant of the alignment of the bars is shown in the version of FIG. 9. Flat sub-gratings $G_{11}$ and $G_{12}$ are used here, while the bars S of the sub-gratings are aligned radially with respect to the focus $F_1$.

Figure 10:
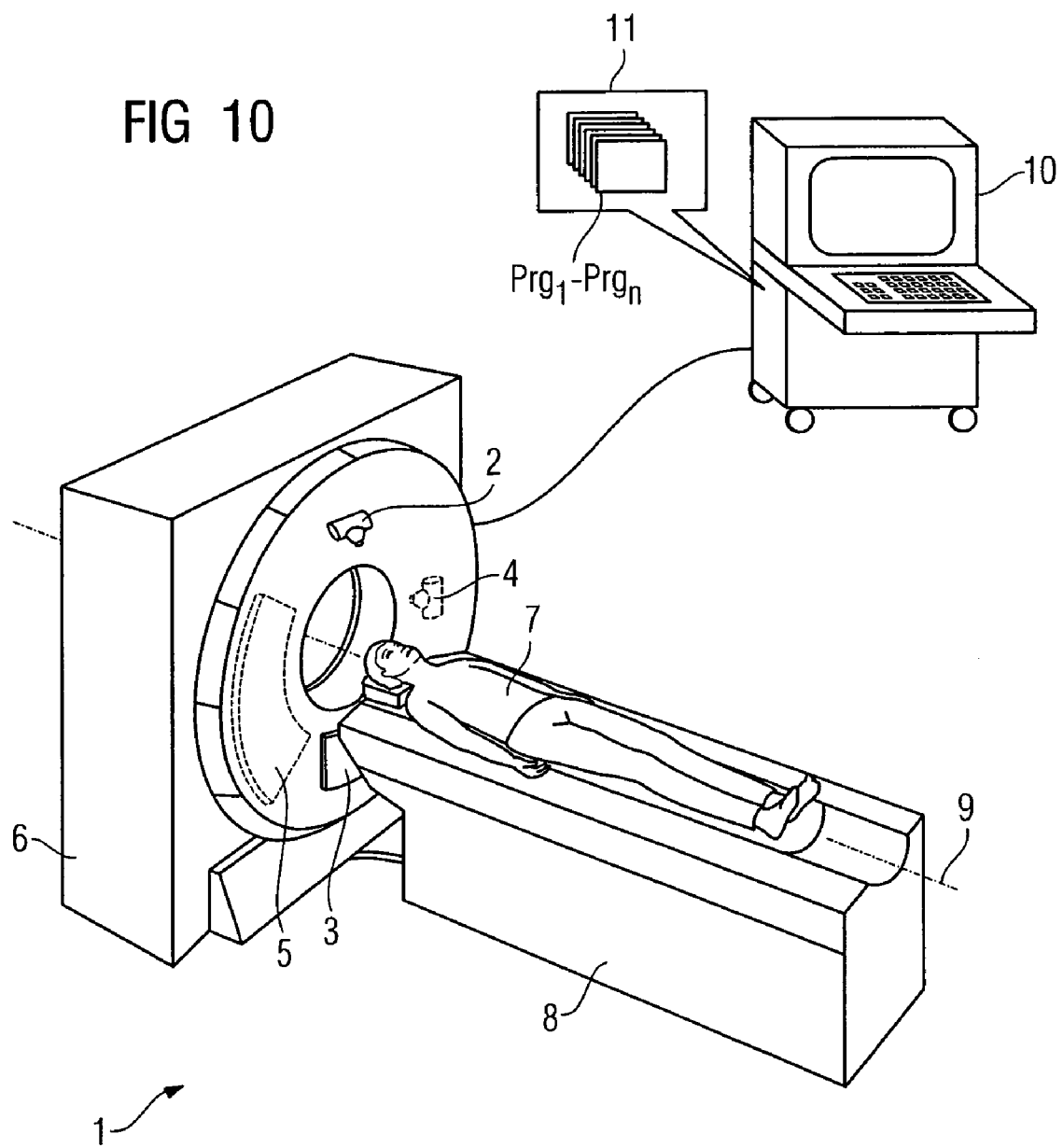
FIG. 10: shows an X-ray computer tomography system in 3D view with a focus-detector system according to an embodiment of the invention.

FIG. 10 represents a complete computer tomography system with focus-detector systems according to an embodiment of the invention for carrying out the method according to an embodiment of the invention, by way of example and also generically for other X-ray systems, in particular X-ray systems for generating projective phase contrast recordings and for C-arc equipment. This figure shows the computer tomography system 1 which includes a first focus-detector system with an X-ray tube 2 and a detector 3 lying opposite, which are arranged on a gantry (not represented in detail) in a gantry housing 6. An X-ray optical grating system according to an embodiment of the invention is arranged in the beam path of the first focus-detector system 2, 3 so that the patient 7, who lies on a patient support 8 displaceable along the system axis 9, can be displaced into the beam path of the first focus-detector system and scanned there. The computer tomography system is controlled by a computation and control unit 10 in which programs $Prg_1$ to $Prg_n$ are stored in a memory 11, which carry out the method according to an embodiment of the invention as described above and reconstruct corresponding tomographic images from the measured ray-dependent phase shifts.

Figure 7:
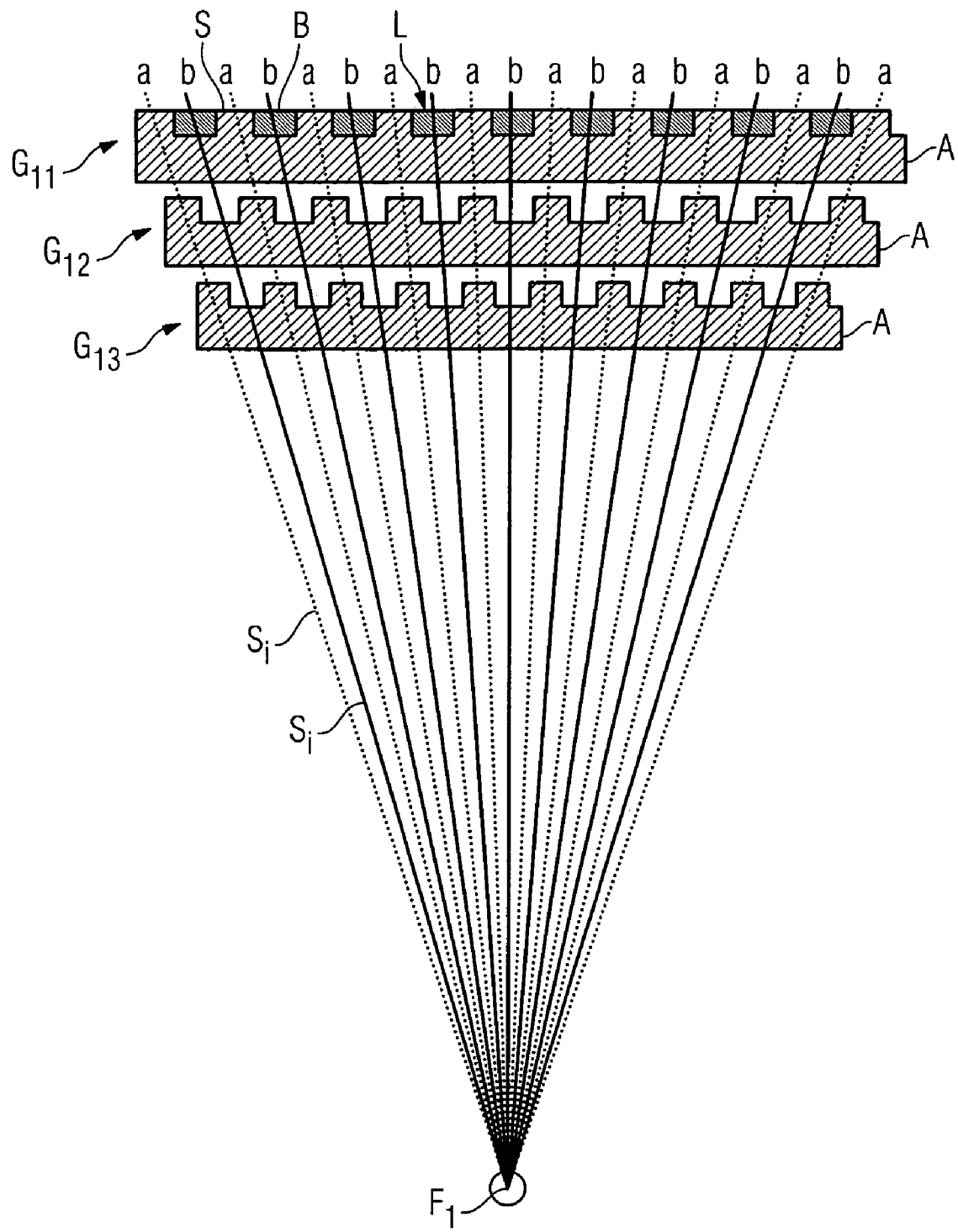
FIG. 7: shows a phase grating according to an embodiment of the invention consisting of three flat sub-gratings, one grating with filler material in the gaps and two gratings without filler material, the gaps and grating bars of the gratings being radially aligned with one another.

Instead of a single focus-detector system, a second focus-detector system may optionally be arranged in the gantry housing. This is indicated in FIG. 7 by the X-ray tube 4 shown in dashes and the detector 5 represented in dashes.

Moreover, it should also be pointed out that the focus-detector systems as presented are not only capable of measuring phase shifts of the X-radiation, rather they are furthermore suitable for conventional measurement of the radiation absorption and the reconstruction of corresponding absorption recordings. Optionally, combined absorption and phase contrast recordings may even be generated.

It is furthermore to be pointed out that the medical computer tomography systems presented in this patent application are merely intended to be an example representation of an alternative application of the invention. AT least one embodiment of the invention may likewise be used in conjunction with systems for examining biological or inorganic samples, without departing from the scope of this application. In particular, at least one embodiment of the invention is applicable to systems for material analysis.

It is to be understood that the features of the invention as mentioned above may be used not only in the combination respectively indicated, but also in other combinations or in isolation, without departing from the scope of the present invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A focus-detector arrangement of an X-ray apparatus for generating at least one of projective and tomographic phase contrast recordings of a subject, comprising:
    a radiation source configured to generate X-radiation and to irradiate the subject;
    a phase grating arranged behind the subject, the phase grating including a plurality of bars with gaps between the plurality of bars, the phase grating being configured to generate an interference pattern of the X-radiation in a predetermined energy range; and
    an analysis-detector system configured to detect at least the interference pattern generated by the phase grating in respect of its phase shift with position resolution, wherein
        in the gaps between the bars, the phase grating includes a filler material having a linear attenuation coefficient in a relevant energy range greater than a linear attenuation coefficient of the bars, and
        a height of the filler material in the gaps is dimensioned so that the X-radiation with an energy and wavelength used for measuring the phase shift generates a phase shift in the X-radiation such that, after the phase grating, rays of the X-radiation which pass through the bars are phase shifted by one half wavelength relative to the rays of the X-radiation which pass through the gaps with the filler material, and is dimensioned so that the attenuation of the X-radiation, at least in relation to the energy used for measuring the phase shift, is the same when passing through the bars and when passing through the filler material.

2. The focus-detector arrangement as claimed in the claim 1, wherein the phase grating is composed of a plurality of sub-gratings arranged in direct succession.

3. The focus-detector arrangement as claimed in claim 2, wherein for each of the sub-gratings, the height of the filler material in the gaps is dimensioned so that the X-radiation with the energy used for measuring the phase shift generates a phase shift by one half wavelength in the X-radiation.

4. The focus-detector arrangement as claimed in the preceding patent claim 3, wherein at least one of the sub-gratings comprises filler material to the height of the bars, at least one of the sub-gratings does not comprise filler material in the gaps, and the height of the entire filler material in gaps arranged above one another in all the sub-gratings is dimensioned overall so that the X-radiation with the energy used for measuring the phase shift generates a phase shift in the X-radiation by one half wavelength, and so that after passing through all the sub-gratings the rays of the X-radiation which pass through the sum of the bars arranged successively in the beam direction have the same intensity loss as the rays of the X-radiation which pass through the sum of the gaps with and without filler material arranged successively in the beam direction.

5. The focus-detector arrangement as claimed in claim 2, wherein the X-radiation used includes at least one of a fan-shaped and conical beam profile, the sub-gratings arranged successively in the beam direction comprise different grating periods, the period spacing of the grating periods increasing from at least one sub-grating to at least one subsequent sub-grating, and the sub-gratings being arranged mutually aligned, such that the rays of the X-radiation pass either only through grating gaps or only through grating bars.

6. The focus-detector arrangement as claimed in claim 1, wherein at least one of the gratings is flat.

7. The focus-detector arrangement as claimed in claim 1, wherein all the gratings are flat.

8. The focus-detector arrangement as claimed in claim 1, wherein at least one of the gratings is curved around a radiation origin in at least one plane.

9. The focus-detector arrangement as claimed in claim 1, wherein all the gratings are curved around a radiation origin in at least one plane.

10. The focus-detector arrangement as claimed in claim 2, wherein the bars and gaps of at least one of the are aligned in the beam direction.

11. The focus-detector arrangement as claimed in claim 2, wherein the bars and gaps of all the gratings are aligned in the beam direction.

12. An X-ray system for generating projective phase contrast recordings, comprising a focus-detector arrangement as claimed in claim 1.

13. An X-ray C-arc system for generating at least one of projective and tomographic phase contrast recordings, comprising a focus-detector arrangement as claimed in claim 1.

14. An X-ray computer tomography system for generating tomographic phase contrast recordings, comprising a focus-detector arrangement as claimed in claim 1.

15. The focus-detector arrangement as claimed in claim 3, wherein the X-radiation used includes at least one of a fan-shaped and conical beam profile, the sub-gratings arranged successively in the beam direction comprise different grating periods, the period spacing of the grating periods increasing from at least one sub-grating to at least one subsequent sub-grating, and the sub-gratings being arranged mutually aligned, such that the rays of the X-radiation pass either only through grating gaps or only through grating bars.

16. The focus-detector arrangement as claimed in claim 4, wherein the X-radiation used includes at least one of a fan-shaped and conical beam profile, the sub-gratings arranged successively in the beam direction comprise different grating periods, the period spacing of the grating periods increasing from at least one sub-grating to at least one subsequent sub-grating, and the sub-gratings being arranged mutually aligned, such that the rays of the X-radiation pass either only through grating gaps or only through grating bars.

17. An X-ray system for generating projective phase contrast recordings, comprising a focus-detector arrangement as claimed in claim 2.

18. An X-ray C-arc system for generating at least one of projective and tomographic phase contrast recordings, comprising a focus-detector arrangement as claimed in claim 2.

19. An X-ray computer tomography system for generating tomographic phase contrast recordings, comprising a focus-detector arrangement as claimed in claim 2.

* * * * *